United States Patent
Seiberg et al.

(10) Patent No.: US 11,020,340 B2
(45) Date of Patent: Jun. 1, 2021

(54) COMPOSITIONS CONTAINING NATURAL PRODUCTS AND USE THEREOF FOR SKIN AND HAIR

(71) Applicant: Seiberg Consulting, LLC, Princeton, NJ (US)

(72) Inventors: Miri Seiberg, Princeton, NJ (US); Konstantinos M. Lahanas, Ramsey, NJ (US)

(73) Assignee: Seiberg Consulting, LLC, Princeton, NJ (US)

( * ) Notice: Subject to any disclaimer, the term of this patent is extended or adjusted under 35 U.S.C. 154(b) by 0 days.

(21) Appl. No.: 15/913,870

(22) Filed: Mar. 6, 2018

(65) Prior Publication Data
US 2019/0083381 A1 Mar. 21, 2019

Related U.S. Application Data

(60) Provisional application No. 62/560,056, filed on Sep. 18, 2017.

(51) Int. Cl.
*A61K 8/9717* (2017.01)
*A61Q 7/00* (2006.01)
*A61Q 3/00* (2006.01)
*A61Q 5/00* (2006.01)
*A61Q 19/08* (2006.01)
*A61K 8/44* (2006.01)
*A61K 36/04* (2006.01)

(52) U.S. Cl.
CPC ............ *A61K 8/9717* (2017.08); *A61K 8/447* (2013.01); *A61K 36/04* (2013.01); *A61Q 3/00* (2013.01); *A61Q 5/002* (2013.01); *A61Q 7/00* (2013.01); *A61Q 19/08* (2013.01)

(58) Field of Classification Search
CPC ...... A61K 8/9717; A61K 8/447; A61K 36/04; A61Q 3/00; A61Q 5/002; A61Q 7/00; A61Q 19/08
See application file for complete search history.

(56) References Cited

U.S. PATENT DOCUMENTS

| | | |
|---|---|---|
| 5,338,673 A | 8/1994 | Thepenier et al. |
| 2005/0065206 A1 | 3/2005 | Kato et al. |
| 2007/0166266 A1 | 7/2007 | Dillon et al. |
| 2009/0069213 A1 | 3/2009 | Avila et al. |
| 2010/0098732 A1 | 4/2010 | Tippens |
| 2013/0288325 A1 | 10/2013 | Liao et al. |
| 2016/0177257 A1 | 6/2016 | Patinier |
| 2017/0135925 A1 | 5/2017 | Seiberg |
| 2017/0172911 A1 | 6/2017 | Hines et al. |

FOREIGN PATENT DOCUMENTS

| | | |
|---|---|---|
| CN | 101862278 | * 10/2010 |
| CN | 104940049 | 9/2015 |
| CN | 104130319 | 7/2017 |
| FR | 2867973 | 9/2005 |
| JP | 0812552 | 1/1996 |
| JP | 2000/319120 | 11/2000 |
| JP | 2002/205950 | 7/2002 |
| JP | 2008137923 | 6/2008 |
| WO | WO 2004/071519 | 8/2004 |
| WO | WO2007/084769 | 7/2007 |
| WO | WO 2009/067095 | 5/2009 |
| WO | WO 2019/055328 | 3/2019 |

OTHER PUBLICATIONS

Chen et al., CN 101862278, published: Oct. 20, 2010, English machine translation obtained on Aug. 17, 2018.*
Wang et al., Environ Health Toxicol., 2014, 29.*
De Jesus Raposo et al., "Bioactivity and Applications of Sulphated Polysaccharides from Marine Microalgae," Mar. Drugs 2013; 11(1):233-252.
Ishikawa et al., "Anti-Melanogenic Activity of Yacon Leaves in Mouse Melanoma Cells," Animal Cell Technology: Basic & Applied Aspects, 2010; 16:359-364.
Rajasulochana et al., "Glimpses on cosmetic applications using marine red algae," IJPT, Sep. 2015; 7(2):9235-9242.
International Search Report and Written Opinion in corresponding PCT Application No. PCT/US 16/60306, dated Jun. 6, 2017, pp. 1-13.
Nadira Binte Samad et al., "In vitro antioxidant and anti-inflammatory activities of Korean blueberry (*Vaccinium corymbosum* L.) extracts," Asian Pac J Trop Biomed 4(10):807-815 (Oct. 2014).
Mei Jing Piao et al., "Antioxidant Effects of the Ethanol Extract from Flower of *Camellia japonica* via Scavenging of Reactive Oxygen Species and Induction of Antioxidant Enzymes," Int. J. Mol. Sci. Apr. 2011, 12:2618-2630.
Mei Jing Piao et al., "Protective Effect of the Ethyl Acetate Fraction of Sargassum muticum Against Ultraviolet B-Irradiated Damage in Human Keratinocytes," Int. J. Mol. Sci. Nov. 2011, 12:8146-8160.
Williamson, "7 Common Causes of Eye Bags & Dark Circles," BIOEFFECT, Oct. 18, 2016, pp. 1-8.
Ines Sjerobabski-Masnec et al., "Skin Aging," Acta Clin Croat 2010; 49:515-519.
International Search Report and Written Opinion in corresponding Application No. PCT/US18/50149, dated Jan. 7, 2019, pp. 1-9.
Extended European Search Report in corresponding Application No. 16866845.7, dated Jul. 8, 2019, pp. 1-11.
Rejane B. Oliveira et al., "Topical anti-inflammatory activity of yacon leaf extracts," Revista Brasileria de Farmacognosia-Brazilian Journal of Pharmacognosy: 23(3):497-505 (2013).
N.N: "Amor Seco," Wikipedia Jun. 26, 2019.
Extended European Search Report in corresponding Application No. 18855933.0, dated Oct. 26, 2020, pp. 1-9.

* cited by examiner

*Primary Examiner* — Genevieve S Alley
(74) *Attorney, Agent, or Firm* — Fish & Richardson P.C.

(57) ABSTRACT

A topical composition comprising a non-denatured, broken-up and dried *Porphyridium* biomass that is not further processed and a pharmaceutically or cosmetically acceptable carrier useful for cosmetic treatments is described.

28 Claims, 2 Drawing Sheets

Treated side        Untreated side (Thinner hair, Lighter color, Shorter eyebrow)

COMPOSITIONS CONTAINING NATURAL PRODUCTS AND USE THEREOF FOR SKIN AND HAIR

BACKGROUND

Skin aging is a slow, chronic process, in which the functionality of skin molecules and structures is reduced with time and is further compromised with UV exposure. Skin aging is first noticed with the appearance of facial sagging, fine lines, wrinkles and age spots, followed by the appearance of dull and thinning hair, sparse eyebrows and eyelashes, and dry and fragile skin and nails. Of a major cosmetic concern are the aging signs around the eye area, because of the importance of the eye area for communication, self-expression and emotional wellbeing.

The anti-aging market provides numerous remedies and solutions directed mainly to enhance facial skin wellness and beauty. Unfortunately, none of these treatments provides a true safe, effective, cost-effective and practical "anti-aging" mean, and consumers keep seeking alternatives. In particular, there is a need for a safe, effective, practical and cost-effective treatment for the aged appearance of the around-eye area, including e.g. "bags" and "dark circles" under the eye, "under-eye hollow" (the preorbital hollow, or tear tough), "crow's feet" on the sides of the eyes, droopy eyelids (ptosis) and "disappearing" eyebrows above the eye.

Consumers and dermatology patients often complain about the appearance of their aged eye area. The general loss of elasticity and skin thickness results in wrinkles and sagging, however several specific around-the-eye aging phenotypes are even more noticed. These include, but are not limited to (1) Under-eye "bags", which are mild swelling or puffiness under the eyes, as the normal fat around the eye descends and creates "bags, (2) "Dark circles", a visible darkening below both eyes, resulting from shadows of volume loss (the periorbital hollows, often called a "tear tough" cast shadows that result in a dark appearance), or loss of dermal extracellular matrix (making the skin thin and translucent, which enables the visibility of the more bluish veins), or imperfections in blood vessels and/or true hyperpigmentation, (3) "Crow's feet", the specific wrinkles and texture changes at the outer corners of the eyes, (4) "Droopy eyelids" (ptosis) where the tissue weakness, loss of volume and downward movement create an old, tired and angry look, and (5) "Disappearing eyebrows", the thinning, lightening and shortening of the eyebrows.

It is desired to have a topical treatment that could prevent, slow, reduce or reverse skin aging, and in particular the aging signs around the eye. It is more desired to have such a treatment as a single and affordable topical treatment for daily care. Such a treatment should provide solutions to skin aging and around-eye aging with little or no irritation and few or no negative side effects and should further provide other desired facial, scalp, body and eye-area skin health, wellness and beautifying benefits. It is further desired to have a topical treatment that does not require a pharmaceutical prescription.

Mammalian hair provides protection, camouflage, temperature control and sexual identity. In contrast, human scalp, beard or mustache hair serve no such functions, and is kept or removed mainly for beauty, cosmetic or social reasons. While eyebrows and eyelashes do function in eye protection, they are more important for human communication and self-expression. Today they are also used in facial recognition technologies for security and monitoring.

Thinning of the hair is a normal process for both men and women. Hair thinning could be induced by many factors, including, but not limiting to diseases (e.g. Atopic dermatitis, Alopecia Areata, Hypothyroidism, autoimmune disease, inflammatory conditions and infection), medications and chemotherapy, malnutrition, or excessive plucking, scrubbing or rubbing. Unfortunately, the most common reason for hair thinning is the natural process of aging. Age-induced hair thinning is a major cosmetic concern, ranging from thin scalp hair, to thinner and shorter eyebrows and eyelashes, to a thin and uneven beard or mustache hair.

Numerous treatments for hair thinning are used as commercial products or home remedies, ranging from naturals (e.g. Amla fruit, Aloe Vera, egg yolks and the like) to OTC drugs (e.g. Minoxidil), all the way to medical procedures like hair transplants.

Unfortunately, none of these treatments provides a true safe, effective, cost-effective and practical mean to affect hair thinning. The cosmetic industry is continuously seeking technologies that could enhance eyebrows, eyelashes, beard, mustache and scalp hair to become thicker, denser, fuller and darker.

It is desired to have a topical treatment that could prevent, slow, reduce or reverse hair thinning. It is more desired to have such a treatment as a single and affordable topical treatment for daily care. Such a treatment should provide solutions to hair thinning with little or no irritation and few or no negative side effects and should further provide other desired health, wellness and beautifying benefits for the hair and its associated skin. It is further desired to have a topical treatment that does not require a pharmaceutical prescription.

Upon aging, nails may become brittle and prone to breaking, may become clubbed (a significant shape-change with very rounded nails), or may be discolored. Unfortunately, there are no consumer products dedicated to nail care, that provide a true safe, effective, cost-effective and practical mean to affect the general health and wellbeing of the nails or to reduce or reverse nail aging. It is desired to have products to enhance the biological properties of the nails and their surrounding skin and cuticle, and to reduce undesired properties associated with nail aging. It is more desired to have products that could prevent, slow, reduce or reverse nail aging. It is desired to have such a product as a single and affordable topical treatment for daily care. Such treatment should provide solutions to aging nails needs, with little or no irritation and few or no negative side effects to the skin, and should further provide other desired health, wellness and cosmetic benefits. It is further desired to have such a single topical treatment that does not require a pharmaceutical prescription.

SUMMARY

The present disclosure features compositions for the topical delivery of a natural product (e.g., to a mammal in need thereof, such as a human) comprising a "broken-up" algae (i.e., the algae is treated so that the cell walls are breached). In one instance, the natural product of this disclosure (1) is non-denatured (e.g., the proteins present in the algae are substantially non-denatured), or (2) contain active, non-denatured catalase and/or glutathione peroxidase, or (3) have a catalase-like activity (e.g., degrading or eliminating hydrogen peroxide), or (4) have a catalase-enhancing activity (e.g., enhancing gene expression, protein translation or other activity that leads to an increase in hydrogen peroxide degradation or elimination), or (5) have a catalase stabilizing activity, or a combination of one or more such activities (collectively defined as "catalase-related activity" or "catalase-like activity"). In another embodiment, the algae could be grown with, or enriched with, or supplemented with, or engineered for producing, or combined with the L-methionine, or the natural products themselves could be combined with L-methionine.

In one embodiment the present disclosure describes a natural product and a pharmaceutical or a cosmetic carrier for topical application. In yet another illustration, the compositions of this disclosure further comprise of delivery system(s), and/or vehicle(s), and/or stabilizing system(s), and/or preservatives that enable to maintain an active catalase-related activity, and deliver such an activity into the skin, the nail or the hair follicles. The compositions described in this disclosure could be used for skin, hair and nail care, to provide skin, scalp, hair and nail with health, wellness and beautifying benefits, and to provide skin, hair and nail with anti-aging benefits. In yet another feature, the compositions described in this disclosure could be used to reduce the visibility of the signs of skin, hair and nail aging.

The compositions described in this disclosure could also be used to preserve the natural health and wellness of the skin, hair or nail, or to slow, or to reduce, or to delay, or to reverse the skin, hair and nail aging process, or to reduce the visibility of the signs of skin, hair and nail aging. Such signs of aging include, but are not limited to facial sagging, fine lines, coarse lines, wrinkles, specific-named facial aging signs (e.g. "crow's feet" (the lines and wrinkles that form around the eyes upon aging), under-eye "bags" and "dark circles" (age-induced, mild puffiness and/or darkening under the eye), "under-eye hollow" (the preorbital hollow, or tear tough), and the like), thinning and shortening of the eyebrows, thinning and shortening of eyelashes, thinning scalp, beard or mustache hair, brittle nails, softer nails and the like. The present disclosure also describes a method of reducing the appearance of aging skin, hair and nail areas of a mammal, said method comprising the step of applying the above compositions to the desired skin, hair or nail areas.

The present disclosure also features a method of reducing the hair thinning process of a mammal, said method comprising the step of applying a composition described herein to the scalp, eyebrows, eyelashes, beard, mustache or to other desired skin areas with hair or to non-glabrous skin.

Hair thinning is defined as the appearance of hair that has changed its density, and/or thickness, and/or length, and/or pigment intensity or shade or color, and/or shine, from the original natural hair status due to biological processes such as aging, chemical exposure, environmental exposure, nutritional exposure, medicine exposure and the like. Human non-glabrous skin is defined as all human skin areas that are hairy, or that can grow hair or that can contain hair follicles. Non-glabrous skin refers to all external skin that is not naturally hairless, and excludes only the skin found on the ventral portion of the fingers, palms, soles of feet, lips, labia minora, and glans penis.

Reducing hair thinning includes, but is not limited to the preservation of the natural thickness of the hair, and/or the density of the hairs, and/or the length of the hair, and/or the shine of the hair, or to reducing the quantity or quality of loss of the natural hair, or to the slowing, reducing, or reversing the process of hair thinning, or to preventing hair thinning, or to reducing the visibility of hair thinning.

In one aspect, the present disclosure relates to methods of preserving the natural status of the hair, or slowing the decay in the natural thinning of the hair, or delaying, or slowing, or reducing the severity of hair thinning, or reducing the appearance of hair thinning, by applying a composition containing a safe and effective amount of a natural product. In another aspect, the natural product could be supplemented with, enriched with or combined with L-methionine.

In another aspect, the present disclosure relates to methods of preventing the decay in the natural growth of the hair and reducing the appearance of hair thinning, by applying a composition containing a safe and effective amount of a natural product. In one aspect the natural product could be supplemented with, enriched with or combined with L-methionine.

In another aspect, the present disclosure relates to methods of partially or completely reversing the decay in the natural growth of the hair and reducing the appearance of hair thinning, by applying a composition containing a safe and effective amount of a natural product. In one aspect the natural product could be supplemented with, enriched with or combined with L-methionine.

In another aspect, the present disclosure features a product including a composition comprising a natural product and instructions directing the user to apply the composition to the hair, scalp, or other skin areas with hair (non-glabrous skin), in order to preserve the natural hair status, or slow, or prevent or reverse the decay in the natural growth of the hair, or slow, or prevent or reverse the appearance of hair thinning. Such hairy skin areas include, but are not limited to the scalp, head, eyebrows, eyelashes, beard, mustache, chest, back, arms, legs and the like.

In another aspect, the present disclosure features a method of promoting a product including a composition containing a natural product by directing the user to apply said composition to the hair, scalp or hairy skin areas, or non-glabrous skin, in order to preserve the natural hair status, or to slow, or prevent or reverse the decay in the natural hair growth, or to slow, or prevent or reverse the appearance of hair thinning.

In another aspect, the present disclosure relates to methods of preserving the natural status of health, wellness and look of the skin, or of slowing the aging of the skin, or of delaying, or slowing, or reducing the severity or the visibility of skin aging signs, or reversing skin aging, by applying a composition containing a safe and effective amount of a natural product. In another aspect the present disclosure relates to methods of preserving the natural status of health, wellness and look of the skin, or of slowing the development of the skin aging process, or of delaying, or slowing, or reducing the severity of the signs of skin aging, by applying a composition containing a safe and effective amount of a natural product. In yet another aspect, the natural product could be supplemented with, enriched with or combined with L-methionine.

In another aspect, the present disclosure relates to methods of partially or completely reversing the aging process of the skin, or reducing the appearance of skin aging signs, by applying a composition containing a safe and effective amount of a natural product. In yet another aspect, the natural product could be supplemented with, enriched with or combined with L-methionine.

In another aspect, the present disclosure features a product including a composition comprising a natural product and instructions directing the user to apply the composition to the affected or desired skin areas, in order to preserve the natural status of health, wellness and look of the skin, or to slow, or prevent, or reverse the skin aging process, or to slow, or prevent or reverse the appearance of signs of skin aging.

In another aspect, the present disclosure features a method of promoting a product including a composition containing a natural product by directing the user to apply said composition to the affected or desired skin areas, in order to preserve the status of health, wellness and look of the skin, or to slow, or prevent or reverse the decay in the aging process of the skin, or to slow, or prevent or reverse the appearance of signs of skin aging.

Described herein is topical composition comprising from about 0.001% to about 25% of a non-denatured, broken-up and dried *Porphyridium* biomass that is not further processed, and a pharmaceutically or cosmetically acceptable carrier, wherein the composition has hydrogen peroxide degrading or eliminating activity. The broken-up *Porphyridium* is *Porphyridium* that has been treated to breach the cell walls and cell membranes. The biomass is not further processed, i.e., is not fractionated or extracted. Thus, essentially the entire content of the *Porphyridium* biomass is present.

In some cases, the composition reduces endogenous keratinocyte hydrogen peroxide levels by at least 20%, 30%, 40% or 50% when the non-denatured, broken-up and dried *Porphyridium* biomass is present at 0.5% w/v (or greater) in the composition.

In some cases, the composition comprises one or more of: a stabilizer, emulsifier, thickener, permeation enhancer, preservative, surfactant, chelating agent, humectant and antioxidant. Other features and advantages of the present disclosure will be apparent from the detailed description of the disclosure and from the claims. It is believed that one skilled in the art can, based upon the description herein, utilize the present disclosure to its fullest extent. The following specific examples are to be construed as merely illustrative and not limitative of the remainder of the disclosure in any way whatsoever. Unless defined otherwise, all technical and scientific terms used herein have the same meaning as commonly understood by one of ordinary skill in the art to which the disclosure belongs. Also, all publications, patent applications, patents, and other references mentioned herein, are incorporated herein by reference. Unless otherwise indicated, a percentage refers to a percentage by weight (e.g. % (w/v)).

FIGURES

DETAILED DESCRIPTION OF THE DISCLOSURE

Figure 1:
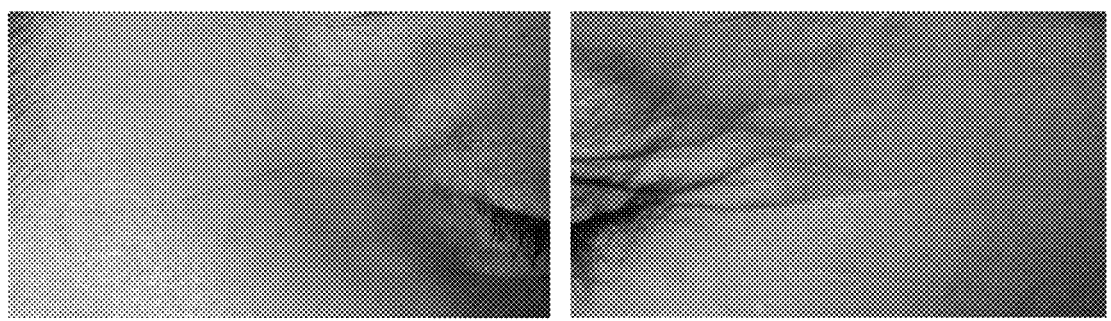
FIG. 1 is a pair of photographs taken before and after the treatment described in Example 5.

The present disclosure relates to the recognition that certain natural products are very effective in the elimination of hydrogen peroxide, and therefore they could be used for preserving the natural status of health, wellness, look and beauty of skin, hair and nail, or for preventing, or slowing, or reducing or reversing the appearance of aging signs of skin, hair and nail.

The red microalgae *Porphyridium* (Genus: *Porphyridium*, including, but not limiting to *Phytoconis purpurea* Bory de Saint-Vincent, 1797, *Porphyridium* Nageli, *Byssus purpurea* Lamarck, *Olivia cruenta* S. F. Gray, *Olivia cruenta* S. F. Gray, *Porphyridium cruentum* (S. F. Gray) Nägeli, *Porphyridium marinum* Kylin, *Sarcoderma sanguineum* Ehrenberg, *Porphyridium* sp. UTEX 637 or a strain derived from *Porphyridium* sp. UTEX 637, *Porphyridium cnientum* UTEX 161 or a strain derived from *Porphyridium omentum* UTEX 161, *Porphyridium aerugineurn* or a strain derived from *Porphyridium aerngineum*, *Porphyridium sordidum* or a strain derived from *Porphyridium sordidum*, or *Porphyridium purpureum* or a strain derived from *Porphyridium purpureum*) is a unicellular red (Rhodophyta) microalga, with cells of 10-20 µM in diameter. Its habitats include fresh water, brackish water, sea water and soil, and it can grow under harsh climate conditions and high UV exposure.

When the microalga is exposed to harsh environmental conditions the cells secret water-soluble sulfated polysaccharides that serve as a protective layer around the cell. These polysaccharides are used as a cosmetic ingredient in skin care products. During the processing of the algae polysaccharides, the algae biomass (the algae cells) is removed and the polysaccharide that was secreted into the growth media is retained for the cosmetic production. The precipitated algae biomass is sometimes considered a waste product, which is discarded during the production of the polysaccharide. The algae are rich in xanthine derivatives, which are sometimes extracted from the biomass for nutritional uses. In some cases, the algae pigments are extracted from the biomass.

It was unexpectedly found that broken-up *Porphyridium* biomass (the broken-up or lysed algae cells ((a composition comprising unfractionated algae cells that have been treated to breach the cell wall) not including the sulfated polysaccharide already secreted into the growth medium) has hydrogen peroxide degrading and eliminating activity. This suggests that *Porphyridium* biomass comprising or consisting essentially of lysed or "broken-up" algae cells (e.g., greater than 20%, 30%, 40%, 50%, 60%, 70%, 80%, 90%, 94%, 96%, 98%, or 99% of the cells lysed or broken-up (or less that 2%, 4%, 6%, 8%, 10%, 15%, 20%, 25%, 30%, 40%, 50%, 60%, 70% or 80% intact algae cells) could be used topically, on skin, scalp, nail and hair, to reduce hydrogen peroxide concentration and provide beneficial effects. The topical use of the broken-up *Porphyridium* biomass should slow, delay, reduce or reverse the progression of skin, hair and nail aging, as well as the visibility of the signs of skin, hair and nail aging.

It is expected that other plants of the family Porphyridiaceae, or of the Phylum Rhodophyta and not only those from the genus *Porphyridium*, would have similar biological properties and that they could also be used in a similar manner. Non-limiting examples of other red microalgae suitable for this disclosure include the unicellular algae of the Bangiophyceae, Florideophyceae, Goniotrichales, *Dixoniella grisea*, or other member of the Rhodophyta.

The precise concentrations, effects of the composition and methods of this disclosure will vary with the area being treated, the age, health and skin and hair type of the end user, the duration and nature of the treatment, the specific composition employed, the particular condition being treated, the particular cosmetically- or pharmaceutically-acceptable carrier utilized, and like factors.

The present disclosure describes a natural product(s) of which (1) is non-denatured (i.e., proteins presented are substantially non-denatured, e.g., by treatment with denaturing heat or denaturing chemicals and/or the hydrogen peroxide elinating activity of the broke up algae is not substantially reduced), or (2) containing active, non-denatured catalase and/or glutathione peroxidase, or (3) is having a catalase-like activity, or (4) is having a catalase-enhancing activity, or (5) is having a catalase-stabilizing activity, or mixtures thereof. The natural product described in this disclosure can be, but is not limited to, a red microalgae powder.

The natural products of this disclosure are powders of broken microalgae. The extracellular secreted polysaccarides are removed, and the microalgae are washed to remove salts of the growth medium, and are then broken-up, or milled, or crushed, or lysed, or pulverized, or minced, or ground, or powdered, or otherwise treated to open (i.e., breach the cell wall and cell membrane) the algae cells, using standard or proprietary procedures. In one instance, there is no extraction, factionation or separation of material. The whole content of the broken-up microalgae is used. In one instance the microalgae are broken-up when they are wet. The broken-up algae "slush" could be then dried using standard conditions, or used "as is". In another instance the algae are dried before they are broken-up. Yet in another instance, the dried broken-up algae powder is size-selected for particles smaller or larger than a desired size, using e.g. any standard filtration or size-selection procedure. In one instance the broken-up algae material is dried (e.g. freeze-dried or spray dried and the like) and is kept in air-tight, sealed and dark containers (e.g. bags, vials and the like) at e.g. room temperature or 40 C or frozen.

In some cases, the material is substantially free of the exopolysaccharides that was secreted by the algae during growth. Such extracellular polysaccharides can be removed by removing the growth media or washing the cells prior to milling or to other treatment that breaks-open or lyses the cells.

In some cases, the color of the broken-up and dried biomass powder could be dark brown, brick red, dark red or dark purple, or a mixture of these colors. In some instances, the color of the broken-up and dried biomass powder that is resuspended in water (0.5-1%) is lighter red, pink, purple, or brown/red, or a combination of these light colors. In one instance, when the broken-up and dried biomass (0.5 or 1%) is resuspended in water, the pH of the resulting mix is from about pH 7 to about pH 8.5. In another instance the pH of the resulting mix is from about pH 7.5 to about pH 8.

In one instance, an enhancement of catalase and/or glutathione peroxidase production within the algae is achieved by (1) selecting relevant genetic variants, or (2) using genetic engineering technologies, or (3) controlling a timed and selective exposure (e.g. continuous, pulsed, at a defined growth phase) to hydrogen peroxide, or (4) controlling a timed and selective exposure to different wavelengths (e.g. UV, blue, or others), or (5) providing certain ingredients (e.g. chemicals, nutritional agents) that impact the growth or the biological properties of the algae, before collecting the algae for processing.

In another instance, the algae (1) could be grown under nutritional conditions that enrich for L-methionine, or (2) could be grown under nutritional conditions that enhance the production of L-methionine, or (3) could be supplemented with L-methionine during growth, or (4) could be engineered to produce or retain L-methionine, or (5) could be combined with L-methionine during the preparation and processing of the natural product. The L-methionine enriched product could be used in all the compositions and methods disclosed herein, and is expected to have superior effects in reducing hydrogen peroxide concentrations in skin, scalp, hair and nail. In one example the enrichment of the growth medium of the algae is with from about 0.1 to about 100 mM L-methionine, which can lead to increased methionine in the algae products prepared from these materials. In addition, or as an alternative, the natural product (e.g. the broken-up, dried *Porphyridium* biomass powder) can be combined with 0.1-100 mM of L-methionine, at any stage of the natural product production and processing.

The effective concentration of L-methionine in the composition should be about the same as the concentration of hydrogen peroxide within the affected tissue (e.g. the skin, hair and nail). This concentration varies with the age, gender, skin type and hair type of the individual, and with their specific need. Lower concentrations (e.g. high micromolar range) would be effective for a very fragile skin, while higher concentrations (e.g. low millimolar range) would be required for affecting hair thinning.

The natural products of this disclosure are non-denatured, and contain stable and active proteins like the catalase enzyme or the glutathione peroxidase enzyme, or the reddish protein-pigment complex Phycoerythrin. "Denaturation" is defined in the Bantam Medical Dictionary (1990 edition) as "the change in the physical and the physiological properties of a protein, that are brought about by heat, X-rays or chemicals. These changes include loss of activity in the case of enzymes". What is meant by "non-denatured product" is a natural product in which the processing for the derivation of such product (e.g., the temperature, the effect of additional ingredients) did not remove or significantly reduce its specific hydrogen peroxide elimination activity. For example, greater than 60%, or greater than 75% or greater than 90% of the hydrogen peroxide eliminating activity that is present in the fresh *porphyridium* biomass is retained in the non-denatured product.

In some instances, the red microalgae powder of the present disclosure is different from other red microalgae cell extracts in two major aspects. First, the dry, non-denatured red algae powder contains all the ingredients of the algae cells, with exception of water, at the same proportions as in the native algae. No algae cell constituent (except water) is removed or is specifically enriched during the processing of the algae, and all components of the algae biomass remain in an "algae powder" preparation that serves as raw material. Second, the red algae powder is kept in its natural, non-denatured state, with all the algae proteins, and in particular those with catalase-like activity, present and active.

In one instance the broken-up algae powder is gamma-irradiated, to reduce the microbial burden of the preparation. The intensity of the gamma irradiation is low (e.g. from about 5 kGy to about 15 kGy) to ensure that the non-denatured state of the powder, or its hydrogen peroxide elimination activity, is not reduced vs. that of the non-irradiated powder.

In one instance the broken-up algae powder, at 0.5% (v/w) in water, has the activity of at least 50% inhibition, namely the removal of at least 50% of the cellular, endogenous hydrogen peroxide, or of at least 50% of the exogenously added hydrogen peroxide.

The natural products of this disclosure can be tested for their hydrogen peroxide eliminating activity using assays like the ROS-Glo™ $H_2O_2$ assay kit (Promega), or the like. The catalase enzyme itself can also be detected and quantified within the natural products using standard procedures, however the existence of the protein does not guarantee its activity, and therefore the activity assays are preferred, and are used to define the natural products.

The novel compositions of this disclosure contain algae powders. The algae are crushed or broken, e.g., they are milled, crushed, abrasively-cut, or broken-up (e.g. by pressure disruption, sonication, jet milling or ball milling, grinding, (e.g. machine grinding, grinding balls, grinding stones, grinding wheels), or lysed, and the like to break cell walls, without creating excessive heat during the process, and are then dried (e.g. lyophilized, spin-dried, spray dried, tray dried, spin flash dried, freeze-dried and the like) at a temperature of about room temperature or at a lower temperature (e.g. 40 C, freezing). The resulting powder could be used in the preparation of natural products that may have from about 0.01% to about 90% by weight dry powder.

In one example, the broken-up algae powder, (e.g. lyophilized, spray dried or freeze-dried and the like) could be suspended in aqueous solutions, with or without filtration or homogenization. In another example, active ingredients could be extracted from the broken algae using aqueous or ethanol/water mixtures, followed by the removal of the ethanol from the extract, in such ways that the specific catalase and/or glutathione peroxidase activity or catalase-related activity of the preparation (the "non-denatured" state) will be retained. Known methods of fractionation could also be used as desired to separate and concentrate the desired activities of this disclosure, or to size fractionate the natural product, or to eliminate inhibitory or undesired activities.

Yet in another example, the fresh or dry algae of this disclosure could be ground or milled or crushed or break-open as described above, suspended in a liquid (e.g. water) and then undergo a mechanical homogenization, or a particle-size reduction (e.g. by sonication, or shear mixing, or homogenization, or any other known semi solid processing, sometimes performed under cold or freezing conditions) to create a homogenate (so that the cells or biomass of the natural source are further broken or disrupted). The resulting suspension could then (1) used as is, or (2) dried and used as a powder, or (3) be further separated (e.g. by centrifugation, or filtration, or by other known procedures), and the supernatant could be further size-selected or separated.

The resulting materials could be used for the compositions of this disclosure "as is", or could be dried-out using standard procedures (e.g. lyophilized, spin-dried, spray dried, tray dried, spin flash dried, freeze-dried and the like) to create a more refined natural product. All such processes should not create unreasonable heat or other conditions that might reduce or eliminate the biological activity of the natural product.

The amount of the algae product in the composition will vary with the area being treated, the age, health and skin and hair type of the end user, the duration and nature of the treatment, the specific composition employed, the particular cosmetically- or pharmaceutically-acceptable carrier utilized, and like factors. For example, in some instances the powder will be used in a liquid form (e.g. a solution or a suspension). Thus, the composition can contain 0.001-99.9%, 0.005-90%, 0.01-50%, 0.05-25%, 0.1-20%, 0.5-20%, 1-10%, 0.01-25%, 0.05-10%, 0.1-5%, and the like, on a volume basis. In some other instances, the algae product will be used in a solid or a powder form or a dried liquid powder form. Thus, the composition can contain 0.001-25%, 0.005-20%, 0.01-10%, 0.05-5%, 0.001-5%, 0.005-10%, and the like, on a weight per volume basis. In some other instances, the amount of the algae product in the composition can be assessed based on the equivalent amount of the algae powder initially used. Such compositions can contain 0.001-25%, 0.005-20%, 0.01-10%, 0.05-5%, 0.001-5%, 0.005-10%, and the like, on a weight per volume basis.

Cosmetic or Pharmaceutical Carrier

Useful compositions can include stabilization systems, which may include one or more preservatives, or one or more anti-oxidants, or one or more chelating agents, or combinations thereof. Preservatives are useful for substantially preventing microbial decomposition. Examples of preservatives include, but are not limited to phenoxyethanol, parabens, commercial compositions such as Diocide (containing Phenoxyethanol, Caprylyl Glycol, Hexylene Glycol) and natural preservatives, and are known to the ones skilled in the art. The composition may comprise from about 0.01% to about 20%, by weight (sometimes more preferably, from about 0.5% to about 5%, by weight) of preservative. Microbial contamination can also be eliminated by gamma irradiation, or electron-beam irradiation, or X-ray irradiation and the like, by microfiltration, or by other standard procedures (e.g. brief heat treatments) that do not result in the elimination of the specific activity described in this disclosure.

Antioxidants and/or chelating agents may also be used to increase shelf life and stability of the compositions. Antioxidants may be added both for formulation stabilization and for biological efficacy. Antioxidant compounds and their derivatives include, but are not limited to, water-soluble antioxidants such as sulfhydryl compounds and their derivatives (e.g., sodium metabisulfite and N-acetyl-cystein), lipoic acid and dihydrolipoic acid, resveratrol, acetyl-cysteine (Iniferine®) or lactoferrin, the commercial Tinogard family of antioxidants, and ascorbic acid and ascorbic acid derivatives (e.g., ascorbyl palmitate and ascorbyl polypeptide). Oil-soluble antioxidants suitable for use in the compositions of this disclosure include, but are not limited to, butylated hydroxytoluene, retinoids (e.g., retinol and retinyl palmitate), tocopherols (e.g., tocopherol acetate), tocotrienols, and ubiquinone. Natural extracts containing antioxidants suitable for use in the compositions of this disclosure, include, but are not limited to, extracts containing flavonoids and isoflavonoids and their derivatives (e.g., genistein and diadzein), extracts containing resveratrol, extracts containing polyphenols and the like. Examples of such natural extracts include, but are not limited to, grape seed, tea, pine bark, Aloe Vera, propolis, or legume extracts. Small molecules with specific antioxidant activity, including, but not limiting to catalase mimetics, SOD mimetics, salem-Mn complexes (e.g. the EUK family of compounds), and the like, are also suitable for use in compositions of this disclosure. Enzymes with specific oxygen-removal activity (e.g. the combination of catalase and glucose oxidase) could also be used on the final formulation or product to remove soluble oxygen and create a nitrogen blanket over the product to reduce oxygen exposure. The compositions of the present disclosure may comprise the antioxidant(s) in an amount of from about 0.001% to about 20%, by weight (e.g., from about 0.01% to about 10%, or from about 0.01% to about 3% by weight) of the composition.

Chelating agents are also useful in assisting the stabilization of compositions. Examples of chelating agents include, but are not limited to EDTA and derivatives thereof (e.g., disodium EDTA and dipotassium EDTA), Iniferine®, lactoferrin, and citric acid. The compositions of the present disclosure may comprise the chelating agent in an amount of from about 0.001% to about 20%, by weight (e.g., from about 0.01% to about 10% by weight) of the composition.

Thickening agents (e.g., thickeners or viscosity enhancing agents) may be used to alter the viscosity of useful compositions. The desired viscosity of the composition will depend upon the intended use (e.g., as a shampoo, conditioner, mousse, cream, lotion, ointment, serum, spray, gel, stick, or the like). For example, in applications such as bath or wash products, the viscosity of the composition should be relatively low, similar to an aqueous solution. Application as a cream, lotion, or gel will have slightly higher viscosity (e.g., between about 100 cps and 100,000 cps). Thickening agents that can be added to the compositions of this disclosure to alter viscosity include polymers such as sepigels or polyacrylates (e.g., polyacrylamide, other carbomers) or polysaccharides (e.g. chitosan). Other examples are commercially ready-made compositions like Aristoflex AVC (containing Ammonium Acryloyldimethyltaurate/VP Copolymer). To achieve the appropriate viscosity, compositions of the present disclosure may comprise from about 0.01% to about 20%, by weight (e.g., from about 0.1% to about 5%, by weight) of a thickening agent.

Additional Cosmetically Active Agents

The compositions containing natural products can also contain other cosmetically active agents (e.g., a synthetic compound(s), or a compound(s) isolated from a natural source, or a natural extract(s) containing a mixture of compounds that has a cosmetic or therapeutic effect on the tissue). The useful compositions described herein may also contain other skin-, hair- and nail-beneficial agents in addition to the natural product(s). Examples of such agents include, but are not limited to, anti-inflammatory agents (such as corticosteroids, NSAIDs, or botanical extracts with anti-inflammatory activity such as Aloe Vera), anti-pruritic agents, topical analgesics, antioxidants (e.g. vitamin C and derivatives, vitamin E and derivatives, botanical extracts with antioxidant activity), agents with catalase-like or SOD-like activity (e.g. salem MN compounds such as the family of EUK agents), epidermal-, dermal- and follicular-regenerating agents and agents that enhance skin, hair and nail, tissue regeneration agents (including e.g. retinoids, retinoid-derivatives, retinol, retinal, alpha hydroxy acids, co-enzyme-Q, growth factors, and others), antibiotics and anti-microbial agents, anti-mycotic agents, anti-yeast agents, anti-parasites, agents that enhance the immune system, dandruff-control and shine-control agents (including e.g. miconazole, ketoconazole, elubiol, itraconazole, coal tar and the like agents), detergents, surfactants, moisturizers, nutrients, vitamins, minerals, energy enhancers, hair or nail growth enhancing agents, agents that delay hair growth, agents for skin conditioning, odor-control agents (such as e.g. odor masking or pH-changing agents), deodorants, antiperspirants, colorants, pigments, color-masking agents, agents that enhance pigment production or pigment delivery (e.g. such as peptides, PAR-2 activators, MC1R ligands, alpha MSH and its mimetics, and the like), agents that enhance or inhibit pigment production, skin lightening agents, agents that affect methionine sulfoxide reductase activity (e.g. L-methionine, that could prevent the oxidation of methionine) and other agents that enhance skin, scalp, hair or nail wellness and beauty that are known to those of ordinary skill in the art.

The useful compositions described herein may also contain compounds that enhance the feel of the composition on the skin, scalp, hair or nail of the user. Examples of such compounds include, but are not limited to, oils, silicones (e.g., siloxane polymers such as dimethicone), polymers, polysaccharides, and skin-conditioning agents such as emollients, and humectants. In addition, the compositions useful herein can contain conventional cosmetic adjuvants, such as e.g. colorants (such as dyes and pigments), opacifiers (e.g., titanium dioxide), and fragrances, which are known to those skilled in the art in the field of this disclosure. The composition and formulations containing such compositions of the present disclosure may be prepared using methodology that is well known by an artisan of ordinary skill.

Forms

The compositions of this disclosure may be used with, but are not limited to, cosmetically or pharmaceutically accepted forms and carriers such as solutions, suspensions, emulsions (including microemulsions and nanoemulsions), lotions, creams, gels, sticks, sprays, ointments, cleansing liquids, washes, solid bars, shampoos, hair conditioners, nail polishes, nail strengtheners, pastes, foams, powders, mousses, shaving creams, shaving gels, wipes, patches, hydrogels, film-forming products, masks, liquid drops, muco-adhesives, and the like.

The compositions of this disclosure may be packaged in a tube, a sealed packet, a jar, a pump, a bottle, a can, a pledget, a towelet, a dispenser, a wipe, a spray can, or the like. An airtight or a light-blocking package (e.g. such as an aluminum tube, aluminum pocket, pump, or laminated tube), can also be used to further enhance product stability.

In one aspect, the compositions of this disclosure further comprise of delivery systems that enable to maintain an active catalase and/or glutathione peroxidase enzyme or catalase-related activity, and deliver the active ingredients, possibly including active proteins, into the hair follicles, or into the nail, or into the skin. Such delivery systems may include micro- and nano-particles, liposomes, aspasomes, organogels, niosomes, transferosomes, patches, micro- and nano-needles, micro- and nano-capsules, micro- and nano-sponges, films, polymers, and the like.

Compositions and Methods

The present disclosure features a method of reducing the hair thinning process of a mammal, said method comprising the step of applying to the scalp, eyebrows, eyelashes, mustache, beard or to other desired non-glabrous skin areas a safe and effective amount of the compositions of this disclosure. The frequency of the application will vary with the area being treated, the age, health, hair type and skin type of the end user, the duration and nature of the treatment, the specific composition employed, the particular cosmetically- or pharmaceutically-acceptable carrier utilized, and like factors. For example, in some instances the application would be periodic, while in other instances the application would be once or twice daily.

Additionally, the present disclosure also features a method of reducing the signs and symptoms of skin, scalp, hair and nail aging and enhancing the biological properties and the health, wellness and beauty of skin, hair and nail, said method comprising the step of applying to the skin, scalp, hair or nail areas in need a safe and effective amount of the compositions of this disclosure. The frequency of the application will vary with the area being treated, the age, health and skin type of the end user, the duration and nature of the treatment, the specific composition employed, the particular cosmetically- or pharmaceutically-acceptable carrier utilized, and like factors. For example, in some instances the application would be periodic, while in other instances the application would be once or twice daily.

As used herein, "safe and effective amount" means an amount of the composition sufficient to induce a desired effect on hair, nail or skin, but low enough to avoid serious side effects. The safe and effective amount of the composition will vary with the area being treated, the age, health, hair type and skin type of the end user, the duration and nature of the treatment, the specific composition employed, the particular cosmetically- or pharmaceutically-acceptable carrier utilized, and like factors.

It is understood that while the disclosure has been described in conjunction with the detailed description thereof, that the foregoing description is intended to illustrate and not limit the scope of the disclosure.

Example 1

A powder of broken-up *Porphyridium* algae was used to create simple prototypes of non-denatured formulations. The dry, non-denatured red algae powder contained all the ingredients of the algae, with exception of water, at the same proportions as in the native algae. No algae constituent (except water) was removed or enriched during the processing of the algae. The red algae powder was kept in its natural, non-denatured state, with all the algae proteins, and in particular those with catalase-like activity, remaining active. The non-denaturing status of the formulation was achieved by avoiding denaturing conditions such as e.g. denaturing agents and heat.

The prototype formulations described in Table 1A purposefully did not contain anti-oxidants or other ingredients usually used to increase shelf life and stability of cosmetic compositions, as the purpose of these prototypes was to evaluate the net activity of the dry algae powder within a usable form. These prototype formulations were used in human proof-of-concept studies as described in following examples. Table 1B describes an example of a similar prototype formulation, which additionally includes antioxidants. Table 1C describes an additional example of a prototype formulation, which additionally includes L-methionine.

TABLE 1A

Prototype formulation A
(broken-up algae powder w/o antioxidants)

| Ingredient | INCI | Percent (W/V) |
| --- | --- | --- |
| Deionized Water | Deionized Water | Up to 100 |
| 1,3 Butylene Glycol | Butylene Glycol | 5.00 |
| Glycerin | Glycerin | 3.00 |
| Diocide | Phenoxyethanol, Caprylyl Glycol, Hexylene Glycol | 1.00 |
| Aristoflex AVC | Ammonium Acryloyldimethyltaurate/ VP Copolymer | 1.00 |
| Broken-up Porphyridium powder | | 0.5, 1.00 |

TABLE 1B

Prototype Formulation B
(broken-up algae powder with antioxidants)

| Ingredient | INCI | Percent (W/V) |
| --- | --- | --- |
| Deionized Water | Deionized Water | Up to 100 |
| Dextrose | Glucose | 0.50 |
| Glucose Oxidase | Glucose Oxidase | 0.05 |
| Catalase | Catalase | 0.05 |
| 1,3 Butylene Glycol | Butylene Glycol | 5.00 |
| NDGA | Nordihydroguaretic Acid | 0.10 |
| Inoveol EGCG | Epigallocatechin Gallatyl Glucoside | 0.05 |
| Glycerin | Glycerin | 3.00 |
| Diocide | Phenoxyethanol, Caprylyl Glycol, Hexylene Glycol | 1.00 |
| Aristoflex AVC | Ammonium Acryloyldimethyltaurate/ VP Copolymer | 1.00 |
| Broken-up Porphyridium powder | | 1.00 |

TABLE 1C

Prototype formulation C
(broken-up algae powder with antioxidants and L-methionine)

| Ingredient | INCI | Percent (W/V) |
| --- | --- | --- |
| Deionized Water | Deionized Water | Up to 100 |
| 1,3 Butylene Glycol | Butylene Glycol | 5.00 |
| Glycerin | Glycerin | 3.00 |
| Diocide | Phenoxyethanol, Caprylyl Glycol, Hexylene Glycol | 1.00 |
| Aristoflex AVC | Ammonium Acryloyldimethyltaurate/ VP Copolymer | 1.00 |
| L-Methionine | L-Methionine | 0.01 |
| Tinogard Q | | 0.05 |
| Tinogard HS | | 0.10 |
| Broken-up Porphyridium powder | | 1.00 |

Example 2

Broken-up algae powders (two independent batches) and the prototype formulations of Table 1A were evaluated for their biological activity in the removal or elimination of hydrogen peroxide by using the ROS-Glo™ $H_2O_2$ assay kit (Promega). The ROS-Glo™ $H_2O_2$ assay is a homogeneous, rapid and sensitive luminescent assay that measures the level of hydrogen peroxide directly in cell culture or in defined reactions. This assay allows identification of conditions or test compounds, such as small molecule inhibitors or inducers that alter ROS levels. An $H_2O_2$ Substrate is employed that reacts directly with $H_2O_2$ to generate a luciferin precursor. Upon addition of ROS-Glo™ Detection Reagent containing Ultra-Glo™ Recombinant Luciferase and Cysteine, the precursor is converted to luciferin by the d-Cysteine, and the produced luciferin reacts with Ultra-Glo™ Recombinant Luciferase to generate a luminescent signal that is proportional to $H_2O_2$ concentration. In the current study $H_2O_2$ was added into the reaction wells and the $H_2O_2$-degrading activity of the test agents, at various concentrations, was evaluated after 30 minutes of exposure at room temperature. Glutathione (GSH) served as a positive control and the luminescence results (RLU) of different GSH concentrations were calibrated to hydrogen peroxide concentrations (see Table 2A). The results of the study are shown in Table 2B.

TABLE 2A

| GSH (%) | microM $H_2O_2$ |
| --- | --- |
| 1.000 | −10.27 |
| 0.800 | −7.13 |
| 0.400 | 14.26 |
| 0.200 | 45.76 |
| 0.100 | 67.84 |
| 0.050 | 105.32 |
| 0.025 | 151.69 |

TABLE 2B

Hydrogen peroxide levels (micromolar) following exposure to different concentrations of test agents Micro Molar $H_2O_2$ (% inhibition)

| % Test agent | GSH | Algae powder 1 | Algae powder 2 | Algae powder formulation of Table 1A |
|---|---|---|---|---|
| 1.000 | −8.278 | 40.452 (79.8) | 37.380 (81.3) | 75.185 (62.4) |
| 0.800 | −6.940 | 49.617 (75.2) | 49.974 (75.05) | 68.338 (66.8) |
| 0.400 | 25.850 | 86.000 (57) | 81.850 (59.1) | 112.349 (43.85) |
| 0.200 | 53.453 | 120.457 (39.7) | 115.718 (42.15) | 127.155 (36.5) |
| 0.100 | 76.093 | 149.549 (25.2) | 148.249 (25.9) | 164.933 (17.5) |
| 0.050 | 112.262 | 167.839 (16.1) | 148.308 925.8) | 182.422 (8.8) |
| 0.025 | 139.566 | 164.147 (17.9) | 172.591 (13.7) | 188.958 (5.5) |

As seen in Table 2B, increasing the concentration of each test agent resulted in a dose-dependent decrease in hydrogen peroxide levels. These data confirm that (1) independent preparations of the broken-up algae biomass powder have the ability to reduce hydrogen peroxide levels in a dose dependent manner and that (2) Formulations of the dry powder of the broken-up algae biomass retained the dose-dependent activity of hydrogen peroxide elimination.

In a similar study, one batch of broken-up *Porphyridium* powder was evaluated for the same biological activity before and after gamma irradiation. The gamma irradiation used was considered weak, and ranged from about 5 to about 15 kGy. The results of this study are presented in Table 2C. This study confirms that applying a low dose of gamma irradiation, known to reduce microorganism burden, has no significant negative effects on the biological activity of the algae powder.

TABLE 2C

Micro Molar $H_2O_2$ (% inhibition)

| % Test/Ref | GSH (%) | Broken-up Porphyridium powder | Gamma-irradiated Broken-up Porphyridium powder |
|---|---|---|---|
| 0.5000 | −9.043 | −7.129 (~100) | −7.223 (~100) |
| 0.2500 | 6.375 | −5.573 (~100) | −5.783 (~100) |
| 0.1000 | 16.548 | −5.276 (~100) | −5.443 (~100) |
| 0.0500 | 28.936 | 2.522 (96.4) | 1.020 (98.57) |
| 0.0250 | 41.413 | 26.686 (61.8) | 25.838 (63.14) |
| 0.0100 | 52.736 | 46.499 (33.57) | 54.949 (21.57) |
| 0.0050 | 49.344 | 59.126 (15.6) | 64.087 (8.57) |
| 0.0025 | 58.797 | 58.844 (16) | 65.109 (7) |

Example 3

A broken-up algae powder preparation was evaluated for biological activity (removal or elimination of hydrogen peroxide) using the ROS-Glo™ $H_2O_2$ assay kit (Promega), as described in Example 2. The powder was suspended in water and used "as is" (non-denatured) for the assay, or was heated to 100 C for 30 minutes to achieve a complete denaturation. Upon heating, the preparation changed its color from red/pink to yellow/green or to light yellow/colorless. The results of this study are shown in Table 3. As documented in Table 3, the non-denatured sample had a significant, dose-dependent activity in reducing hydrogen peroxide concentration. In contrary, the denatured sample of the same powder preparation showed only very little activity at the higher test concentrations, and was almost inactive at the lower test concentrations. This result suggests that the majority of the hydrogen peroxide elimination activity of the *Porphyridium* biomass powder is heat-sensitive, and that the biomass powder should be kept in a non-denatured condition for its use in skin, hair and nail care.

TABLE 3

Micro Molar $H_2O_2$ (% inhibition)

| % test agent | GSH | Algae powder, Non-denatured | Algae powder, denatured |
|---|---|---|---|
| 0.8 | −14.5708 | 75.21217 (67.6) | 122.8012 (43.5) |
| 0.4 | −14.384 | 123.308 (46.8) | 206.8614 (4.9) |
| 0.2 | 10.87454 | 153.0173 (34) | 176.7401 (18.7) |
| 0.1 | 53.42675 | 178.7979 (22.96) | 190.3407 (12.5) |
| 0.05 | 98.15699 | 206.9203 (10.85) | 192.0861 (11.7) |
| 0.025 | 141.3439 | 231.324 (0.43) | 200.9237 (7.6) |
| 0 | 233.8936 | 232.1353 (0) | 217.5366 (0) |

Example 4

Epidermal equivalents (EPI-200, MatTek) were exposed to increasing doses of UVB-irradiation (100-400 mJ/cm2). Following UVB-irradiation, tissues were incubated for additional 24 hours before the collection of the culture media for evaluation of PGE2 secretion. PGE2 is an inflammatory marker, which is induced by UV and is associated with skin aging and with certain skin diseases. As seen in Table 4A, UV exposure induced a significant, dose-dependent release of PGE2 from the epidermal equivalents.

Next, the epidermal equivalents were treated daily with the broken-up *Porphyridium* formulations of Example 1, for 72 hours, prior to exposure to UVB-irradiation of 200 mJ/cm2. The test materials included the base formulation of Table 1 (with no algae material), formulations of Table 1 containing 1% and 0.5% of the broken-up biomass powder, and a 1:10 dilution in PBS of the 1% formulation. Following UVB-irradiation, tissues were treated once more with the formulations, and at 24 hours following the last treatment the culture media were collected for evaluation of PGE2 secretion. The results of this study are shown in Table 4B. These results document a marked reduction in UV-induced PGE2 secretion upon treatment with the broken-up biomass formulations.

These results indicate that a formulation of the broken-up *Porphyridium* powder could reduce the harmful effects of UV on the skin. This suggests that the broken-up *Porphyridium* powder could be useful in treating human skin exposed to UV irradiation, and in protecting from, or in reversing processes involved in skin aging and certain skin diseases.

TABLE 4A

| Treatment | Average PGE2 Concentration (pg/mL) | Std Dev |
|---|---|---|
| Untreated + Sham | 8093.058 | 3357.481 |
| Untreated + 100 mJ/cm2 UVB | 11862.76 | 2916.228 |
| Untreated + 200 mJ/cm2 UVB | 15009.18 | 3623.92 |
| Untreated + 300 mJ/cm2 UVB | 22864.30 | 4640.584 |
| Untreated + 400 mJ/cm2 UVB | 38601.73 | 9783.425 |

TABLE 4B

| Treatment | Average PGE2 Concentration (pg/mL) | StDev |
|---|---|---|
| Base Formulation + 200 mJ/cm2 UVA/UVB | 7282.871 | 716.1853 |
| 1% broken-up formulation + 200 mJ/cm2 UVA/UVB | 6244.65 | 5389.626 |
| 0.5% broken-up formulation + 200 mJ/cm2 UVA/UVB | 4922.62 | 1834.175 |
| 1:10 dilution of 1% broken-up formulation + 200 mJ/cm2 UVA/UVB | 7573.963 | 3641.33 |

Example 5

The broken-up algae powder formulation of Table 1A, containing 1% dry broken-up algae powder, was used to treat the "crow's feet" area of the right eye of a post-menopausal, Caucasian female. The "crow's feet" area of the left eye remained untreated. Both areas were equally treated with a sunscreen on a need basis, but with no other topical treatments. Treatment was performed twice daily for three months. At time 0, 2 and 3 months, photographs of the two "crow's feet" areas were recorded and compared (FIG. 1). These photographs documented a visible and significant reduction in both the fine lines and the coarse lines of the "crow's feet" on the treated side, with no improvement on the untreated side, at both 2 and 3 months of treatment. These data document the anti-aging activity of the dry broken-up algae powder in significantly reversing the "crow's feet" signs of aging.

Example 6

Figure 2:
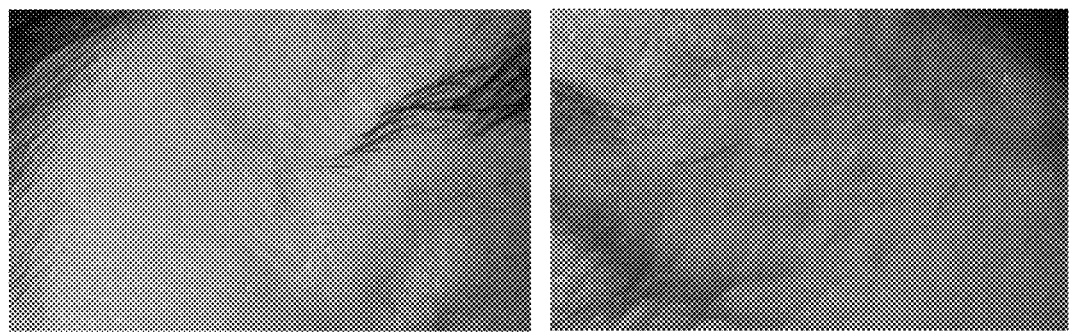
FIG. 2 is a pair of photographs taken before and after the treatment described in Example 6.

The broken-up algae powder formulation of Table 1A, containing 1% dry broken-up algae powder, was used to treat the right eyebrow of a post-menopausal, Caucasian female. The left eyebrow remained untreated. Both eyebrows were equally treated with a sunscreen on a need basis, but with no other topical treatments. Treatment was performed twice daily for three months (FIG. 2). At time 0, 2 and 3 months, photographs of the two eyebrows were recorded and compared. These photographs documented a visible and significant hair thickening on the treated eyebrow, resulting in a thicker, fuller, darker and a little longer eyebrow, with no such changes on the untreated side, at both 2 and 3 months of treatment. These data document the activity of the dry broken-up algae powder in reversing hair thinning and creating a thicker, fuller and longer eyebrow.

The invention claimed is:

1. A topical composition comprising from about 0.1% (w/v) to 20% (w/v) of a non-denatured, broken-up and dried *Porphyridium* biomass that is not further processed, fractionated or extracted and is not exposed to denaturing heat or denaturing chemicals and wherein the proteins present in the biomass are substantially non-denatured, a thickening agent and a pharmaceutically or cosmetically acceptable carrier, wherein the composition has hydrogen peroxide degrading or eliminating activity.

2. The composition of claim 1, wherein the composition further comprises L-methionine.

3. The composition of claim 1, wherein the *Porphyridium* was grown under conditions that enrich for L-methionine.

4. The topical composition of claim 1, wherein the thickening agent is present at 0.01% (w/v) to 20% (w/v).

5. A method for reducing hair thinning, comprising applying the topical composition of claim 1 to non-glabrous skin.

6. The method of claim 5, wherein the application is to the scalp, eyebrow, eyelashes, beard or mustache.

7. The method of claim 5, wherein the composition further comprises L-methionine.

8. The method of claim 5, wherein the *Porphyridium* was grown under conditions that enrich for L-methionine.

9. The method of claim 5, wherein applying the composition reduces hydrogen peroxidase concentration in the scalp and non-glabrous skin.

10. The method of claim 5, wherein the method (i) slows the thinning of hair, (ii) preserves natural hair thickness and density, (iii) reverses the thinning of hair, and/or (iv) delays the thinning of hair.

11. A method for reducing the appearance of skin aging in a subject, comprising applying to skin the topical composition of claim 1.

12. The method of claim 11, wherein the composition further comprises L-methionine.

13. The method of claim 11, wherein the *Porphyridium* algae was grown under conditions that enrich for L-methionine.

14. The method of claim 11, wherein the sign of skin aging is wrinkles.

15. The method of claim 11, wherein the sign of skin aging is sagging.

16. The method of claim 11, wherein the sign of skin aging is fine lines.

17. The method of claim 11, wherein the sign of skin aging is coarse lines.

18. The method of claim 11, wherein the sign of skin aging is crow's feet.

19. The method of claim 11, wherein the sign of skin aging is under-eye bags.

20. The method of claim 11, wherein the sign of skin aging is dark circles.

21. The method of claim 11, wherein the sign of skin aging is droopy eyelids.

22. The method of claim 11, wherein the sign of skin aging is the preorbital hollow or tear trough.

23. The method of claim 11, wherein the sign of skin aging is thinning of eyebrows.

24. The method of claim 11, wherein applying the composition reduces hydrogen peroxidase concentration in the skin.

25. The method of claim 11, wherein the method (i) slows the progression of skin aging, (ii) preserves natural skin health, wellness and beauty, (iii) reverses the development and progression of skin aging, and/or (iv) delays the development and progression of skin aging.

26. A method for improving the appearance or strength of nails in a subject, comprising applying to nails the composition of claim 1.

27. The method of claim 26, wherein the composition further comprises L-methionine.

28. The method of claim 26, wherein the *Porphyridium* algae was grown under conditions that enrich for L-methionine.

* * * * *